(12) United States Patent
Biedermann

(10) Patent No.: US 11,160,592 B2
(45) Date of Patent: Nov. 2, 2021

(54) METHOD OF USING BONE PLATE WITH POLYAXIAL INJECTION SCREWS

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 110 days.

(21) Appl. No.: 16/655,699

(22) Filed: Oct. 17, 2019

(65) Prior Publication Data
US 2020/0121373 A1  Apr. 23, 2020

Related U.S. Application Data

(60) Provisional application No. 62/747,367, filed on Oct. 18, 2018.

(51) Int. Cl.
| A61B 17/86 | (2006.01) |
| A61B 17/80 | (2006.01) |
| A61B 17/88 | (2006.01) |
| A61B 17/56 | (2006.01) |
| A61B 17/70 | (2006.01) |

(52) U.S. Cl.
CPC ........ *A61B 17/864* (2013.01); *A61B 17/8057* (2013.01); *A61B 17/863* (2013.01); *A61B 17/8615* (2013.01); *A61B 17/8805* (2013.01); *A61B 17/7098* (2013.01); *A61B 2017/564* (2013.01); *A61B 2017/8655* (2013.01)

(58) Field of Classification Search
CPC .............. A61B 17/864; A61B 17/8877; A61B 17/8047; A61B 17/8605; A61B 17/7098; A61B 17/8014; A61B 17/8042; A61B 17/8057; A61B 17/8805

USPC ......................... 606/304, 291, 281
See application file for complete search history.

(56) References Cited

U.S. PATENT DOCUMENTS

| 4,044,512 A | 8/1977 | Fischer et al. |
| 5,725,581 A | 3/1998 | Branemark |

(Continued)

FOREIGN PATENT DOCUMENTS

WO   WO2017/074275 A1   5/2017

OTHER PUBLICATIONS

Flow-Screw Surgical Technique Guide, Flow-FX, LLC, 2016, STG-102 Rev A.

(Continued)

*Primary Examiner* — Marcela I. Shirsat
(74) *Attorney, Agent, or Firm* — Gordon & Jacobson, P.C.

(57) ABSTRACT

A method is provided for stabilizing a bone. A plate is positioned over a bone. The bone plate has a polyaxial screw hole with a spherically curved seat. A bone hole is formed beneath the screw hole. A screw having a head with a spherical outer surface, and a threaded shaft with an internal cannula and a plurality of fenestrations is provided. The screw is driven through the first screw hole and into the bone hole until the outer surface of the head is supported by the spherically curved screw seat. A syringe provided with a needle is inserted into the internal cannula of the shaft of the screw. The syringe includes a bone injectable material that is injected through the needle, into the internal cannula, and out of at least one fenestration into the bone. After injection, the needle is removed from the screw shaft.

16 Claims, 4 Drawing Sheets

(56) References Cited

U.S. PATENT DOCUMENTS

| | | | |
|---|---|---|---|
| 5,743,912 A | 4/1998 | Lahille et al. | |
| 5,788,702 A | 8/1998 | Draenert | |
| 5,871,484 A | 2/1999 | Spievack et al. | |
| 6,048,343 A | 4/2000 | Mathis et al. | |
| 6,214,012 B1 | 4/2001 | Karpman et al. | |
| 6,554,830 B1 | 4/2003 | Chappius | |
| 6,565,572 B2 | 5/2003 | Chappius | |
| 6,635,059 B2 | 10/2003 | Randall et al. | |
| 6,755,835 B2 | 6/2004 | Schultheiss et al. | |
| 6,863,671 B1 | 3/2005 | Strobel et al. | |
| 6,918,912 B2 | 7/2005 | Seemann | |
| 6,989,014 B2 | 1/2006 | Justin et al. | |
| 7,037,309 B2 | 5/2006 | Weil et al. | |
| 7,250,055 B1 | 7/2007 | Vanderwalle | |
| 7,261,716 B2 | 8/2007 | Strobel et al. | |
| 7,300,439 B2 | 11/2007 | May | |
| 7,338,493 B1 | 3/2008 | Vandewalle | |
| 7,354,442 B2 | 4/2008 | Sasso et al. | |
| 7,488,320 B2 | 2/2009 | Middleton | |
| 7,608,097 B2 | 10/2009 | Kyle | |
| 7,717,947 B1 * | 5/2010 | Wilberg | A61B 17/864 606/304 |
| 7,731,738 B2 | 6/2010 | Jackson et al. | |
| 7,892,265 B2 | 2/2011 | Perez-Cruet et al. | |
| 7,951,179 B2 | 5/2011 | Matityahu | |
| 8,231,632 B1 | 7/2012 | Jordan et al. | |
| 8,382,808 B2 | 2/2013 | Wilberg et al. | |
| 6,214,012 C1 | 10/2013 | Karpmen et al. | |
| 8,574,273 B2 * | 11/2013 | Russell | A61B 17/8605 606/304 |
| 8,808,335 B2 * | 8/2014 | Biedermann | A61B 17/8877 606/291 |
| 8,821,506 B2 | 9/2014 | Mitchell | |
| 8,945,193 B2 | 2/2015 | Kirschman | |
| 8,992,587 B2 | 3/2015 | Kirschman | |
| 9,155,580 B2 | 10/2015 | Cormier et al. | |
| 9,265,540 B2 | 2/2016 | Kirschman | |
| 9,265,548 B2 | 2/2016 | Jones et al. | |
| 9,333,018 B2 | 5/2016 | Russell et al. | |
| 9,993,276 B2 | 6/2018 | Russell | |
| 2009/0157078 A1 | 6/2009 | Mikol | |
| 2010/0298889 A1 | 11/2010 | Wilberg et al. | |
| 2013/0184765 A1 * | 7/2013 | Beyar | A61B 17/80 606/281 |
| 2015/0320462 A1 * | 11/2015 | Biedermann | A61B 17/8047 606/291 |

OTHER PUBLICATIONS

N-Force Fixation System Surgical Technique, Zimmer Biomet, 2017, 0208.1-GLBL-en-REV0517.

Philos with Augmentation Surgical Technique, DePuy Synthes, 2016.

\* cited by examiner

METHOD OF USING BONE PLATE WITH POLYAXIAL INJECTION SCREWS

CROSS-REFERENCE TO RELATED APPLICATION

This application claims benefit to U.S. Provisional Ser. No. 62/747,367, filed Oct. 18, 2018, which is hereby incorporated by reference herein in its entirety.

BACKGROUND OF THE INVENTION

1. Field of the Invention

The present invention relates to surgery. More particularly, the invention relates to systems and methods of bone fixation using bone plates and screws.

2. State of the Art

Bone plates and screws are well-known for treating bone fractures and loss of integrity of a bone. However, in some circumstances the bone includes osseous voids, which threaten the structural integrity of the bone. Such voids are caused by trauma, infection, congenital malformation, tumor growth, or degenerative diseases. Where such voids are located there will be limited or insufficient purchase of the screw in the bone for appropriate stabilization during healing.

It has been described to treat such bone structure with a cannulated fenestrated screw through which a bone cement can be injected during the plating procedure to enhance stabilization. For example, as described in WO 2017/074275, a plate is provided with a cannulated fenestrated bone screw. The bone screw has a generally cylindrical head and an inner groove. The generally cylindrical head is presumably adapted to engage at a fixed angle within a corresponding hole in the bone plate to direct the screw at a predetermined angle relative to the bone plate. The inner groove is for attachment of an apparatus that can inject bone cement into the screw, through an axial channel of the bone screw, and out of the screw and into the poor-quality bone. After the cement is injected into the bone, it expands and hardens and thereby stabilizes the treatment site.

SUMMARY OF THE INVENTION

A method is provided for stabilizing a bone fracture using a system including a bone plate with a plurality of polyaxial screw holes, at least one cannulated fenestrated polyaxial screw, and a locking element to lock an angle of the polyaxial screw relative to the bone plate.

The plate includes an upper side, a bone-contacting lower side, and the plurality of polyaxial screw holes extending through the plate between the upper and lower sides. The polyaxial screw holes each include a first portion open at the upper side with an upper thread for engagement with the locking element and a lower annular shoulder, a conical portion flaring open toward the lower side of the plate, and a spherically curved seat portion located between the first portion and the conical portion. In an embodiment, the central axis of the seat portion is angularly offset relative to the central axis of the first portion, and the central axis of the conical portion is aligned with the seat portion. This screw hole configuration permits the polyaxial screw to be inserted at an increased angle of inclination relative to a Zero-position; i.e., when the shaft of the screw is aligned coaxially relative to a central axis of the first portion. More preferably, the polyaxial screw holes are adapted to permit insertion of the screw up to at least around 20° with respect to the Zero-position of the screw in the seat corresponding to a total range of motion of up at least 40°, with an even greater angle of inclination to one side; i.e., the direction at which the seat portion is angularly offset, while simultaneously providing a low profile in terms of a low thickness and a high angular stability.

The cannulated fenestrated polyaxial screw includes a head and a shaft. The head has an outer surface forming at least a portion of a sphere and a proximal driver slot. The shaft has an external helical bone-engaging thread, an internal cannula, a closed distal end at a distal end of the cannula, and an axial arrangement of fenestrations extending generally radially from the inner cannula to the exterior of the shaft. The system may optionally also include at least one non-fenestrated polyaxial screw, and may optionally include at least one fixed-angle screw.

The locking element includes an external thread and a lower spherically-curved recess. The locking element is adapted to be positioned into the threaded first portion of the screw hole to lock the angular and axial position of the screw relative to the plate.

The system also includes a syringe with a needle sized to be received within the cannula of the cannulated fenestrated polyaxial screw. The syringe preferably is loaded with a bone injectable material, such as bone void filler, bone cement, bone growth material, bone strengthening agent, antibiotic or anti-infective agent, or other beneficial agent for the treatment at weakened bone, diseased bone and/or a fracture. The needle is sized to extend to the distal end of the cannula. The syringe and needle are adapted to inject bone injectable material into the cannulated fenestrated polyaxial screw after the shaft of the cannulated fenestrated polyaxial screw is fully seated into the bone and head of the screw is fully seated in the seat portion of the plate. Preferably, neither the needle nor the syringe are adapted to attach to the head of the cannulated fenestrated polyaxial screw.

In a method of using the system, the plate is positioned over the bone to be treated. Holes are drilled at a desired angle within a range of angles into the bone underlying the screw holes using a pilot drill. A cannulated fenestrated polyaxial screw is driven through the polyaxial screw hole into the bone. The cannulated fenestrated polyaxial screw is driven until the head of the screw seats fully within the seat of the screw hole.

The syringe, filled with the bone injectable material, is provided. The needle of the syringe is advanced into and through the cannula of the cannulated fenestrated polyaxial screw to at or near the distal end of the screw. The syringe is operated to inject the bone injectable material out of the needle, into the cannula, out of a distal fenestration of the cannulated fenestrated polyaxial screw, and into the bone. As the bone injectable material flows out of the syringe, into the bone, and fills pores in the bone surrounding the distal end of the cannulated fenestrated polyaxial screw, the needle is retracted proximally in the cannula to cause the bone injectable material to flow out of a relatively proximal fenestration. The method continues until the bone injectable material fills the intended area of bone surrounding the cannulated fenestrated polyaxial screw. The needle is then drawn proximally out of the cannula. In order to permit the needle to moved relative to the cannula, it is specifically required that neither the syringe nor the needle be attached to the cannulated fenestrated polyaxial screw during delivery of the bone injectable material.

In an embodiment, after the bone injectable material has been delivered and the syringe and needle withdrawn from the cannulated fenestrated polyaxial screw, the locking element is positioned into the threaded first portion of the screw hole and driven into contact with the head of the screw to compress the screw between the locking element and the screw seat of the screw hole to securely lock the angular and axial position of the screw relative to the plate.

In another embodiment, substantially similar to that described above, the locking element includes a central opening adapted to receive the needle therethrough. In such embodiment, the locking element can be inserted into the screw hole after the cannulated fenestrated polyaxial screw is seated and driven to securely lock the angular and axial position of the screw relative to the plate prior to injection of the bone injectable material.

In either embodiment, the method may also include inserting additional cannulated fenestrated polyaxial screws and injecting bone injectable material through such screws. Further, the method may also include inserting non-fenestrated polyaxial screws and optionally locking the orientation of such screws with respective locking caps; inserting fixed angle compression screws; and inserting fixed angle locking screws, all relative to the bone plate. The additional screws may be inserted at any time during the procedure.

DETAILED DESCRIPTION OF THE PREFERRED EMBODIMENTS

Figure 1:
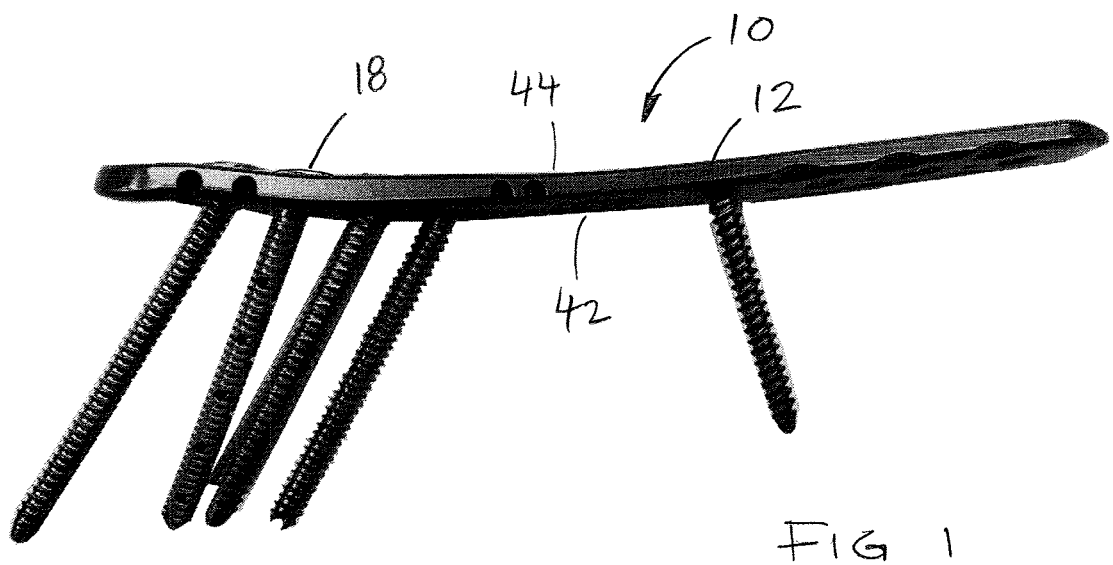
FIG. 1 is a side elevation of a bone plate system.
Figure 2:
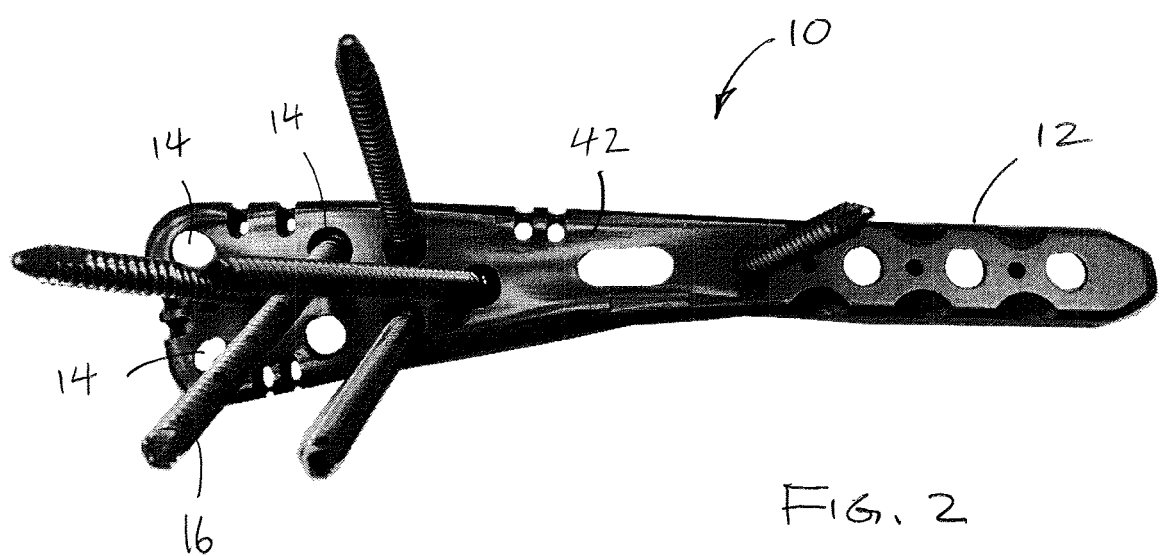
FIG. 2 is a bottom view of the bone plate system of FIG. 1.
Figure 3:
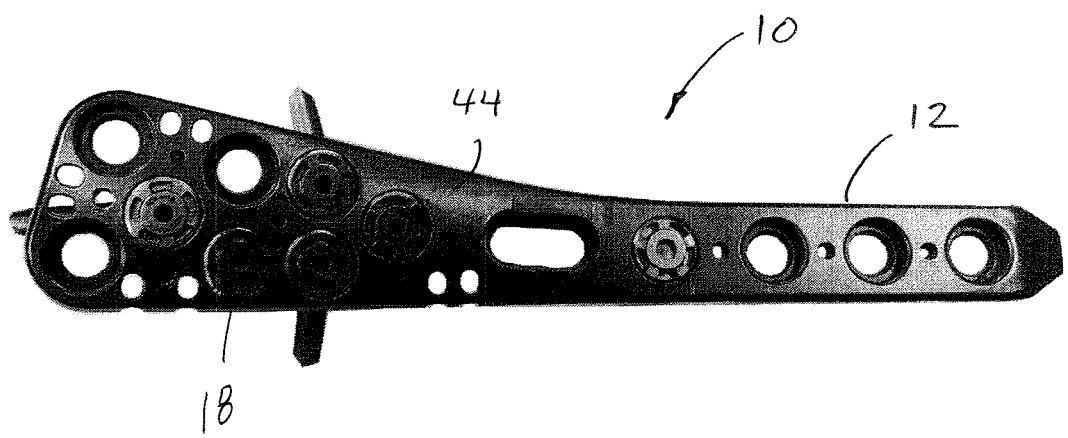
FIG. 3 is a top view of the bone plate system of FIG. 1.

Turning now to FIGS. 1 through 3, in accord with an aspect of a method for stabilizing a bone fracture, a system 10 is provided including a bone plate member 12 with a plurality of polyaxial screw holes 14, at least one cannulated fenestrated polyaxial bone screw 16, and a locking element 18 to lock an angle and axial position of the cannulated fenestrated polyaxial bone screw 16 within and relative to one of the polyaxial screw holes 14 of the bone plate member 12.

Figure 4:
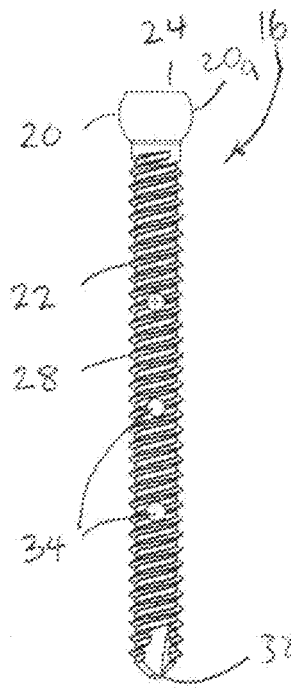
FIG. 4 is a side elevation of a cannulated fenestrated polyaxial bone screw for the system described herein.
Figure 5:
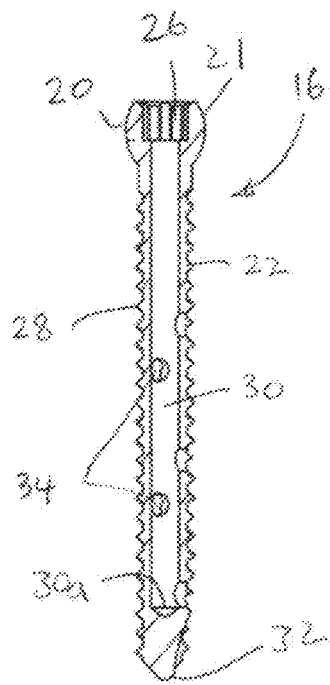
FIG. 5 is a longitudinal section view along axis S of the cannulated fenestrated polyaxial bone screw of FIG. 4.
Figure 6:
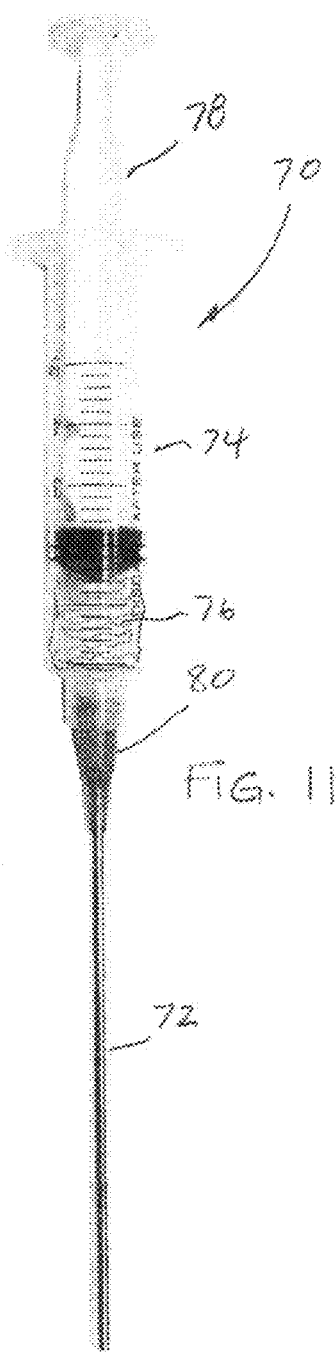
FIG. 6 is a longitudinal section view of a cannulated non-fenestrated polyaxial bone screw for the system described herein.
Figure 7:
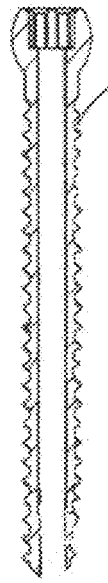
FIG. 7 is a longitudinal section view of a solid polyaxial bone screw for the system described herein.
Figure 8:
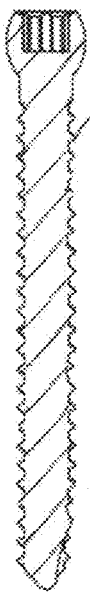
FIG. 8 is a longitudinal section view of a fixed angle bone screw for the system described herein.

Referring to FIGS. 4 and 5, the cannulated fenestrated polyaxial bone screw 16 includes a head 20 and a shaft 22. The head 20 has an outer surface 21 forming at least a portion of a sphere, a flat upper surface 24, and a proximal axial driver slot 26 (FIG. 5) formed in the upper surface 24. The shaft 22 has an external helical bone-engaging thread 28, an internal cannula 30 (FIG. 5) meeting the driver slot 26, a preferably closed distal end 32 at a distal end 30a (FIG. 5) of the cannula 30, and a longitudinal displacement of fenestrations 34. The fenestrations 34 are openings extending from the internal cannula 30 to the exterior of the shaft 22. The fenestrations 34 preferably extend radially outward perpendicular to a longitudinal shaft axis S (FIG. 4) of the shaft 22, but may extend along a polar angle of displacement, at a distal angle, or at a proximal angle relative to the shaft axis S. The fenestrations 34 may be of a common size, or of various sizes such that, e.g., smaller fenestrations are provided relatively distally, and larger fenestration are provided relatively proximally along the shaft 22, or vice versa. The system 10 can additionally include at least one non-fenestrated bone screw, such as cannulated polyaxial screw 16a (FIG. 6) or non-cannulated polyaxial bone screw 16b (FIG. 7), and/or one or more fixed-angle bone screw, such as screw 16c (FIG. 8) with a threaded head portion 20c (FIG. 8).

Turning back to FIGS. 1 through 3, the plate member 12 of the system includes a bone-contacting lower side 42 and an opposing upper side 44. The plurality of polyaxial screw holes 14 extend through the plate member 12 from the upper side 44 to the lower side 42. The plate member 12 is sized, shaped and contoured at at least its lower side 42 such that, in an embodiment, it is particularly well-adapted to be implanted adjacent a periarticular, such as at a metaphysis of a bone, and has its screw holes 14 positioned for directing cannulated fenestrated polyaxial bone screws 16 into underlying bone for stabilization of such anatomy. The plate member 12 may be adapted for treating a fracture of an upper extremity, such as, by way of example, a proximal humerus plate (as shown), or a lower extremity, such as, by way of example, a distal tibia plate. The plate member 12 may also be adapted for other bones of the body, such as, by way of example, a pelvic plate.

Figure 9:
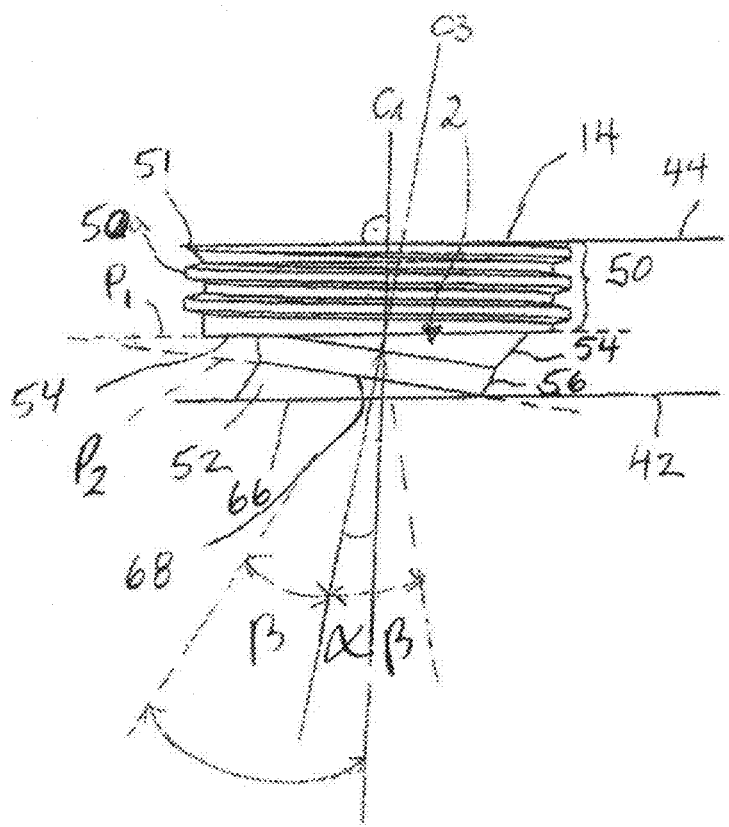
FIG. 9 is a cross-sectional view of a polyaxial screw hole adapted to a permit screw angulation toward a favored side.

Referring to FIG. 9, the polyaxial screw holes 14 each includes a first portion 50, a second portion 52, a third portion 54, and a seat portion 56, described as follows with respect to one embodiment of the system 10. The first portion 50 is open to the upper side 44 of the plate member 12 and has a surrounding edge 51. In an embodiment, the first portion 50 has a circular cross-section bounded by the edge 51. An internal thread 50a is provided within the first portion 50 for engagement by the locking element 20. The internal thread 50a may extend the full axial length or along a partial length of the first portion 50. The first portion 50 generally extends into the plate member 12 about half-way between the upper and lower sides 44, 42 (one-half plate thickness) where it ends at a lower annular shoulder 54 which defines a first plane P1. The first portion 50 defines a central axis C1 through the first portion 50 and perpendicular to the first plane P1.

The second portion 52 is conical and flares open toward the lower side 42 of the plate member 12. The second portion 52 defines a circular or elliptical edge 66. The diameter of the second portion 52 is at least equal to the smallest diameter of the seat portion 56, with an increasing inner diameter towards the open end of the lower side 42 of the plate member 12.

The seat portion 56 is preferably adapted to fully circumferentially support the head 20 of the cannulated fenestrated polyaxial bone screws 16. The seat portion 56 is formed by a hollow spherical segment-shaped portion that extends between the first portion 50 and the second portion 52 with a decreasing inner diameter towards the second portion 52. A central axis C3 of symmetry extends through the seat portion 56. In an embodiment permitting an increased angulation of the screw shaft 22 toward a favored direction, the seat central axis C3 is inclined with respect to the central axis C1 of the first portion 50 by an angle α. In this embodiment, angle α is approximately 10°; angle α can be other angles. (Where no particular direction of angulation is favored, the seat central axis C3 can be coaxial with the central axis C1 of the first portion 50.) The seat central axis C3 intersects the central axis C1 at a position in the screw hole 14 that corresponds to the center point of the sphere defined by the spherical seat portion 56. By the tapering design of the seat portion 56, an inwardly extending annular edge 68 is formed between the seat portion 56 and the second portion 52. The inwardly extending annular edge 68 defines the smallest diameter of the screw hole 14. Moreover, the inwardly extending annular edge 68 defines a second plane P2 perpendicular to the seat central axis C3. The second plane P2 is tilted relative to the first plane P1 and intersects the first plane P1 at the angle α. A Zero-position (0°-position) of the cannulated fenestrated polyaxial bone screw 16 is defined by the shank axis S being coaxial to the seat central axis C3.

The lowermost portion of the seat portion 56 may extend partially to the lower side 42 of the plate member 12. Alternatively, the lowermost portion of the seat portion 56 may be located at some distance from the lower side 42. The uppermost portion of the seat portion 56 can be at the first plane P1 or can merge into the first portion 50.

Additionally, the third portion 54 of the screw hole 14 is arranged between the first portion 50 and the seat portion 56 and connects them. The diameter of the third portion 54 is equal to or more than the largest diameter of the head 20 of cannulated fenestrated polyaxial bone screw 16 and may be smaller than the diameter of the first portion 50. The head 20 may be guided by the third portion 54 when it is inserted.

The maximum angle of inclination that the shank axis S can assume with respect to the seat central axis C3 may be defined by the diameter of the first portion 50 of the screw hole 14 relative to the largest outer diameter of the screw head 20 and the size and position of the engagement structure for a driver adapted to rotationally drive the cannulated fenestrated polyaxial bone screw 16, such as a standard hex driver. Additionally, the width of the second portion 52 may limit the maximum angle of inclination. The pivot angle of the cannulated fenestrated polyaxial bone screw 16 in the seat portion 56 or the insertion angle of the bone screw 16 around the seat central axis C3 is an angle β resulting in a total range of motion of 2β.

Since the seat central axis C3 defines the Zero-position of the cannulated fenestrated polyaxial bone screw 16 as mentioned above, the bone screw 16 is angled at the angle α relative to the central axis C1 of plane P1 in its Zero-position. Hence, the shank axis S of the cannulated fenestrated polyaxial bone screw 16 is already angled with respect to the central axis C1 of the first portion 50 to the favored side in the Zero-position, which is 10° in this embodiment. Depending on the size of the first portion 50 of the screw hole 14, and due to the design of the second portion 52 of the screw hole 14, it is possible to insert the cannulated fenestrated polyaxial bone screw 16 into the bone at an angle of β relative to its Zero-position to a favored side. Consequently, the shank axis S of cannulated fenestrated polyaxial bone screw 16 may be inclined to the favored side with a maximum angle that is the sum α+β, which may be around 30° relative to the central axis C1 of the plane P1. As the motion cone is circular and thus symmetrical about the central axis C3, the angle of inclination to the side opposite from the favored side is reduced by the angle α starting from the bone screw's Zero-position and thus is β-α in total. This, however, is not detrimental as the favored side is intended to be used for the angular position of the cannulated fenestrated polyaxial bone screw 16.

Other embodiments of the polyaxial screw hole 14 can permit a lesser or an even greater maximum angle to a favored side, and can be used as a substitute for, or in addition to, the polyaxial screw hole 14 described above. Furthermore, the plate member 12 may have a plurality of holes of the same type or may have one or more polyaxial screw holes of different design.

The plate member 12 may also have one or more fixed angle screw holes that restrict the angular direction of a screw head within the screw hole and the shaft extension beyond the lower side 42 of the plate member 12. Such holes may have a portion that is cylindrical in shape or is tapered to a decreasing inner diameter toward the open end of the lower side 42 of the plate member 12. The plate member 12 may also have one or more screw holes adapted for receiving a screw with a threaded head, such as the fixed-angle bone screw 16c shown in FIG. 8, in a fixed angle engagement. Such screw holes have an inner helical thread or other engagement structure adapted to directly engage an outer helical thread or other engagement structure on the head of the screw. Such screws holes do not require a spherical seat, and can be cylindrical or conical, and/or stepped in their diameters. Such screws are generally not used with the locking element 18, described below. The plate member 12 may also have one or more screw holes of any of type suitable for stabilization of a bone fracture, damaged bone, or diseased bone.

Figure 10:
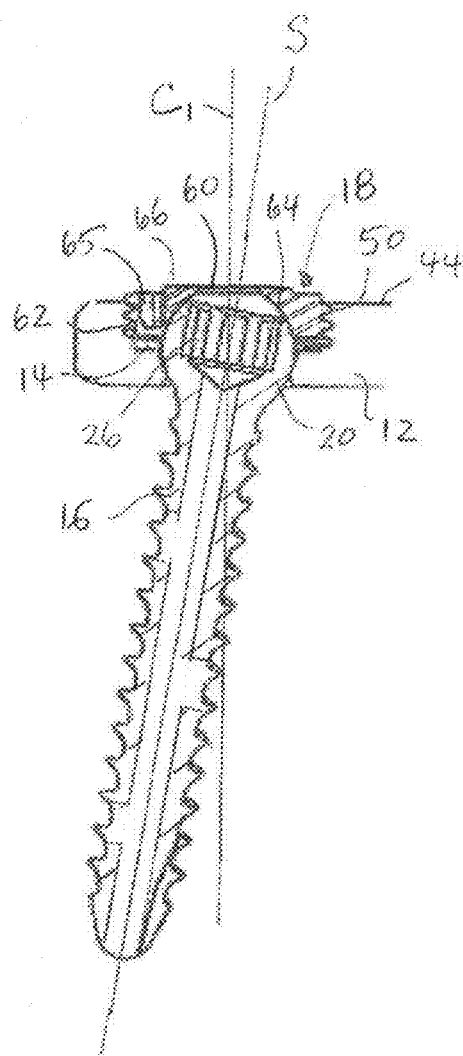
FIG. 10 is a cross-sectional view through a plate member, a polyaxial bone screw, and a locking element.

Turning now to FIG. 10, the locking element 18 is adapted to be positioned into the threaded first portion 50 of the screw hole 14 to lock the angular and axial position of the cannulated fenestrated polyaxial bone screw 16 relative to the plate member 12. The locking element 18 is substantially cylindrical with a diameter that corresponds to the diameter of the first portion 50 of the screw hole 14. The locking element 18 has an external thread 62 for engaging the thread 50a in the first portion 50 of the screw holes 14, a lower spherically-curved recess 64 for accommodating at least of a portion of the screw head 20, and at least one further recess 65 provided for engagement with a driver. The height of the locking element 18 is preferably smaller than the depth of the first portion 50 so that the top side 66 of the locking element 18 can sit substantially flush with the upper side 44 of the plate member 12 when the head 20 of the cannulated fenestrated polyaxial bone screw 16 is locked by the locking element 18.

Figure 11:
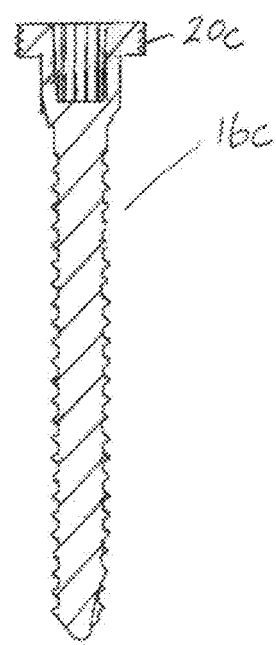
FIG. 11 is a syringe filled with a bone injection material, which is part of the system described herein.

Referring to FIG. 11, the system 10 also includes a syringe 70 with a needle 72. The syringe 70 includes a barrel 74 preferably loaded with a bone injectable material 76, a plunger 78 displaceable within the barrel 74, and a nozzle 80 at the end of the barrel 74 connected to the needle 72. The needle 72 is sized to be received within the inner cannula 30 of the cannulated fenestrated polyaxial bone screw 16. For purposes herein, the term "needle" does not require that the distal end of such structure be sharp, but it must be a substantially rigid, open, tubular member of small diameter for insertion into the head 20 of the cannulated fenestrated polyaxial bone screw 16 and adapted to carry the bone injectable material from the nozzle 80 of the syringe 70 to the cannulated fenestrated polyaxial bone screw 16. The bone injectable material 76 is preferably a bone void filler, bone cement, bone growth material, bone strengthening agent, antibiotic or anti-infective agent, or other beneficial agent for the treatment at weakened bone, spongy or porous bone, diseased bone and/or fractured bone. The movement of the plunger 78 through the barrel 74 will force bone injectable material out of the barrel 74, through the nozzle 80, and out of the needle 72. Preferably, neither the syringe 70 nor needle 72 are adapted to attach to the head 20 of the cannulated fenestrated polyaxial bone screw 16.

Figure 12:
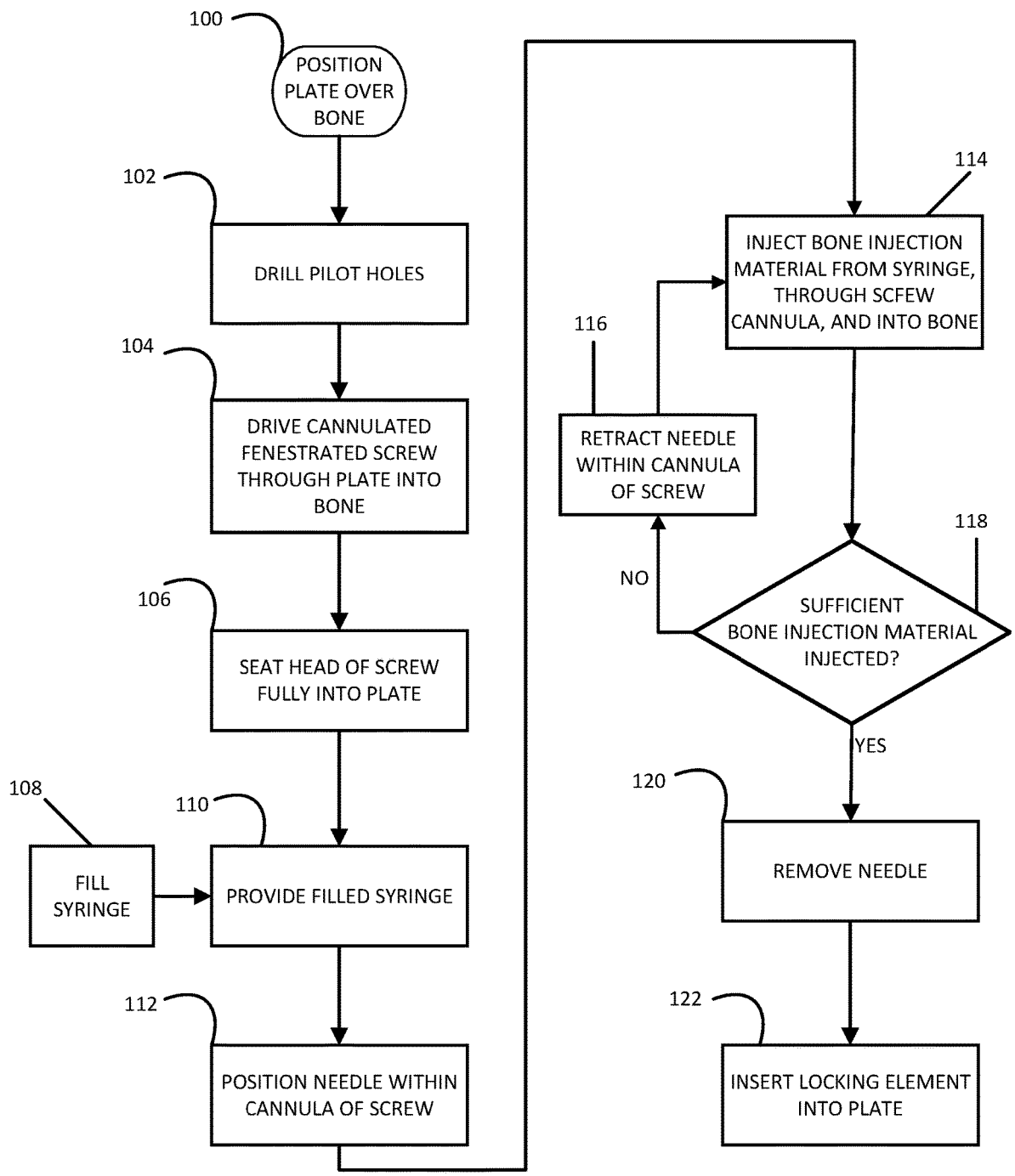
FIG. 12 is a flow chart illustrating a method described herein.

Now, turning to FIG. 12 and in accord with a method of using the system 10, the plate member 12 is positioned at 100 over the bone to be treated. Holes are drilled at 102 with a standard pilot drill at a desired angle within a range of angles into the bone underlying the screw holes. The cannulated fenestrated polyaxial bone screw 16 is driven at 104 through the polyaxial screw hole 14 in the plate member 12 and into the bone. The cannulated fenestrated polyaxial bone screw 16 is driven at 106 until the head 20 of the screw 16 seats fully within the seat portion 56 of the screw hole 14 and is preferably recessed below the upper side 44 of the plate member 12.

It is anticipated that the bone surrounding the cannulated fenestrated polyaxial bone screw 16 is not sufficiently supportive for the screw 16 and/or plate member 12 due to the quality of bone. Therefore, it is desirable to buttress the quality of the bone with a bone injected material 76. The cannulated fenestrated polyaxial bone screw 16 and bone injectable material 76 permit such quality enhancement.

The barrel 74 of the syringe 70, if not previously filled with the bone injectable material, is filled at 108 with the bone injectable material 76 by removing the plunger 78 to provide access to the barrel 74. After the desired amount of bone injectable material is placed in the barrel 74, the plunger 78 is re-positioned in the barrel 74. The filled syringe 70 is provided at 110.

The needle 72 of the syringe 70 is then advanced at 112 into the cannula 30 of the cannulated fenestrated polyaxial bone screw 16, preferably, though not necessarily, to at or near the distal end 32 of the screw 16. The plunger 78 of the syringe 70 is displaced to inject the bone injectable material 76 at 114 out of the distal end of the needle 72, into the screw cannula 30, out of a distal fenestration 34 of the cannulated fenestrated polyaxial bone screw 16, and into the poor-quality bone surrounding the screw 16. As the bone injectable material 76 flows out of the syringe 70 and into the bone, and fills the bone surrounding the distal end 32 of the cannulated fenestrated polyaxial bone screw 16 and the inside of the distal end 30a of the cannula 30, the needle 72 is retracted proximally at 116 within the cannula 30 and relative to the screw 16 to cause the bone injectable material 76 to flow out of a relatively proximal fenestration 34. The method continues at 118 until the bone injectable material 76 sufficiently fills the intended area of bone surrounding the cannulated fenestrated polyaxial bone screw 16. The needle 72 is then retracted out of the cannula 30 at 120. In order to permit the needle 72 to move relative to the cannula 30, it is specifically required that neither the syringe 70 nor the needle 72 be attached to the cannulated fenestrated polyaxial bone screw 16 during delivery of the bone injectable material 76.

After the bone injectable material 76 has been delivered and the syringe 70 and needle 72 withdrawn from the cannulated fenestrated polyaxial bone screw 16, the locking element 18 is positioned at 122 into the threaded first portion 50 of the screw hole 14 and driven into contact with the head 20 of the screw 16 to compress the screw 16 between the locking element 18 and the seat portion 56 of the screw hole 14. This securely locks the angular and axial position of the cannulated fenestrated polyaxial bone screw 16 relative to the plate member 12.

In another embodiment, substantially similar to that described above, the locking element 18 includes a central opening 60 adapted to receive the needle 72 therethrough. In such embodiment, the locking element 18 can be inserted into the screw hole 14 after the cannulated fenestrated polyaxial bone screw 16, and driven to securely lock the angular and axial positions of the screw 16 relative to the plate member 12 prior to injection of the bone injectable material 76.

In either embodiment, the method may also include inserting additional cannulated fenestrated polyaxial screws 16 and injecting bone injectable material 76 through such screws 16; inserting non-fenestrated polyaxial screws and optionally locking the orientation of such screws with respective locking elements 18; inserting fixed angle compression screws; and inserting fixed angle locking screws, all relative to the bone plate member 12. The additional screws may be inserted at any time during the procedure.

There have been described and illustrated herein embodiments of a polyaxial injection screw system and methods of using such system. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A method of stabilizing a bone, comprising:
   a) positioning a bone plate member over a bone, the bone plate member having a lower surface adapted to be in contact with the bone and an opposing upper surface, a polyaxial screw hole extending between the upper and lower surfaces, the polyaxial screw hole including a screw seat with a spherically curved surface, and at least a fixed angle screw hole extending between the upper and lower surfaces, the fixed angle screw hole defining a central axis;
   b) forming a bone hole beneath the fixed angle screw hole;
   c) driving a fixed angle screw into the fixed angle screw hole, the fixed angle screw having a head and a shaft, the head engaging the fixed angle screw hole to retain the shaft coaxial with the central axis of the fixed angle screw hole;
   d) forming a bone hole beneath the polyaxial screw hole;
   e) driving a cannulated fenestrated polyaxial screw through the first polyaxial screw hole and into the bone hole, the cannulated fenestrated polyaxial screw including a head and a shaft,
      the head having an outer surface forming at least a portion of a sphere and a driver slot, and
      the shaft having an external helical bone-engaging thread, an internal cannula meeting the driver slot, and a longitudinal displacement of fenestrations extending from the internal cannula to an exterior of the shaft,
      the cannulated fenestrated polyaxial screw driven until the outer surface of the head is supported by the spherically curved surface of the screw seat;
   f) providing a syringe filled with a bone injectable material, the syringe provided with a needle;

g) after driving, inserting the needle into the internal cannula of the shaft of the cannulated fenestrated polyaxial screw;

h) after inserting, injecting the bone injectable material from the syringe into the internal cannula and out of at least one fenestration into the bone; and i) removing the needle from the shaft of the cannulated fenestrated polyaxial screw.

2. The method of claim 1, further comprising:
prior to removing the needle, retracting the needle within the internal cannula and injecting the bone injectable material from the syringe into the internal cannula and out of at least another fenestration into the bone.

3. The method of claim 1, wherein the polyaxial screw hole has an upper portion with a thread defining a first central axis, and the screw seat defines a second central axis angulated relative to the first central axis, and the screw shaft of the cannulated fenestrated polyaxial screw has a shaft axis extending at a non-zero angle relative to the second central axis.

4. The method of claim 3, wherein the shaft axis extends at a non-zero angle relative to the first central axis.

5. The method of claim 1, wherein the injecting occurs without coupling the needle relative to the cannulated fenestrated polyaxial screw such that the needle can be longitudinally displaced relative to the internal cannula.

6. The method of claim 1, wherein the outer surface of the head of the cannulated fenestrated polyaxial screw is recessed below the upper surface of the plate member during the injecting.

7. The method of claim 1, wherein:
after removing the needle, locking a locking element within the polyaxial screw hole and over the head of the cannulated fenestrated polyaxial screw to lock the angle of the cannulated fenestrated polyaxial screw relative to the plate member.

8. The method of claim 7, wherein:
the polyaxial screw hole has an upper portion provided with a threaded portion, and the locking element includes an external thread that engages the threaded portion.

9. The method of claim 1, further comprising inserting a second polyaxial screw with a head and shaft,
wherein the bone plate member has at least a second polyaxial screw hole having an upper portion provided with a threaded portion and a lower portion provided with spherically curved screw seat, and
the second polyaxial screw is inserted into the second polyaxial screw hole until the head of the second polyaxial screw seats within the spherically curved screw seat of the second polyaxial screw hole.

10. The method of claim 9, wherein the second polyaxial screw is a cannulated, fenestrated screw.

11. The method of claim 9, wherein the second polyaxial screw is a non-fenestrated screw.

12. The method of claim 1, further comprising inserting a third screw with a head and shaft,
wherein the bone plate member has at least a third screw hole with a screw seat, and
the shaft of the third screw is inserted through the third screw hole and into the bone until the head of the second third screw seats against the screw seat of the third screw hole and applies a compressive force on the plate member between the plate member and the bone.

13. The method of claim 1, wherein the bone injectable material is a bone void filler.

14. The method of claim 1, wherein the bone injectable material is a bone cement.

15. The method of claim 1, wherein the bone injectable material includes an anti-infection agent.

16. A method of stabilizing a bone, comprising:
a) positioning a bone plate member over a bone, the bone plate member having a lower surface adapted to be in contact with the bone and an opposing upper surface, a polyaxial screw hole extending between the upper and lower surfaces, the polyaxial screw hole including a screw seat with a spherically curved surface, and at least a fixed angle screw hole extending between the upper and lower surfaces, the fixed angle screw hole defining a central axis;

b) forming a bone hole beneath the fixed angle screw hole;

c) driving a fixed angle screw into the fixed angle screw hole, the fixed angle screw having a head and a shaft, the head engaging the fixed angle screw hole to retain the shaft coaxial with the central axis of the fixed angle screw hole;

d) forming a bone hole beneath the polyaxial screw hole;

e) driving a polyaxial screw through the polyaxial screw hole and into the bone hole, the polyaxial screw including a head and a shaft,
the head having an outer surface forming at least a portion of a sphere and a driver slot, and
the shaft having an external surface with a bone-engaging thread, an internal cannula meeting the driver slot and in fluid communication with the external surface via a fluid pathway, and a closed distal end,
the polyaxial screw driven until the outer surface of the head is supported by the spherically curved surface of the screw seat;

f) providing a syringe filled with a bone injectable material, the syringe provided with a needle;

g) after driving, inserting the needle into the internal cannula of the shaft of the polyaxial screw;

h) after inserting, injecting the bone injectable material from the syringe into the internal cannula and out of the fluid pathway into the bone; and i) removing the needle from the shaft of the polyaxial screw.

* * * * *